(12) United States Patent
Kirchner et al.

(10) Patent No.: US 9,326,833 B2
(45) Date of Patent: May 3, 2016

(54) METHOD AND A SYSTEM IN THE PREPARATION OF A DENTAL RESTORATION, A MEASURING ELEMENT AND USE THEREOF

(75) Inventors: Bastian P. Kirchner, Fürstenfeldbruck (DE); Malte Korten, Gröbenzell (DE); Josef A. Waizenegger, Seefeld (DE); Sebastian Guggenmos, Peissenberg (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 817 days.

(21) Appl. No.: 13/510,529

(22) PCT Filed: Nov. 19, 2010

(86) PCT No.: PCT/US2010/057315
§ 371 (c)(1),
(2), (4) Date: Sep. 21, 2012

(87) PCT Pub. No.: WO2011/063169
PCT Pub. Date: May 26, 2011

(65) Prior Publication Data
US 2013/0004919 A1   Jan. 3, 2013

(30) Foreign Application Priority Data
Nov. 19, 2009   (EP) .................................... 09176460

(51) Int. Cl.
*A61C 8/00* (2006.01)
*A61C 9/00* (2006.01)
*A61C 13/00* (2006.01)

(52) U.S. Cl.
CPC .............. *A61C 8/005* (2013.01); *A61C 9/0053* (2013.01); *A61C 13/0004* (2013.01); *A61C 8/0001* (2013.01)

(58) Field of Classification Search
None
See application file for complete search history.

(56) References Cited

U.S. PATENT DOCUMENTS

| | | | |
|---|---|---|---|
| 4,908,017 A | 3/1990 | Howson | |
| 5,176,646 A | 1/1993 | Kuroda | |
| 5,464,128 A | 11/1995 | Keller | |
| 5,807,334 A | 9/1998 | Hodosh | |
| 2004/0204787 A1 | 10/2004 | Kopelman | |
| 2006/0019219 A1* | 1/2006 | Saliger et al. | 433/173 |
| 2006/0106484 A1* | 5/2006 | Saliger et al. | 700/182 |
| 2008/0176188 A1* | 7/2008 | Holzner et al. | 433/215 |

(Continued)

FOREIGN PATENT DOCUMENTS

| | | |
|---|---|---|
| WO | WO 97/30654 | 8/1997 |
| WO | WO 2009/065954 | 5/2009 |

*Primary Examiner* — Sean Shechtman
*Assistant Examiner* — Steven Garland

(57) ABSTRACT

A method in the preparation of a dental restoration, in which the dental restoration has an implant unit and a head structure interconnectible with one another, comprises the steps of providing an auxiliary material, providing a computerized head receiving surface representation (A'), manufacturing from the auxiliary material a measuring element having a measuring surface (M) and an implant unit coupling surface (X). The measuring surface (M) is adapted such that it can be captured by an optical measuring device, and the measuring element coupling surface (X) is adapted for mating with the head receiving surface (A). The method may help making the preparation of a dental restoration more time and cost efficient.

12 Claims, 7 Drawing Sheets

(56) References Cited

U.S. PATENT DOCUMENTS

| | | |
|---|---|---|
| 2009/0042167 A1 | 2/2009 | Van Der Zel |
| 2009/0087817 A1* | 4/2009 | Jansen et al. .................. 433/223 |
| 2009/0104583 A1* | 4/2009 | Yau et al. ...................... 433/213 |
| 2009/0111071 A1* | 4/2009 | Yau et al. ...................... 433/173 |
| 2010/0021859 A1* | 1/2010 | Kopelman ...................... 433/50 |
| 2011/0136080 A1 | 6/2011 | Holzner |

\* cited by examiner

METHOD AND A SYSTEM IN THE PREPARATION OF A DENTAL RESTORATION, A MEASURING ELEMENT AND USE THEREOF

CROSS REFERENCE TO RELATED APPLICATIONS

This application is a national stage filing under 35 U.S.C. 371 of PCT/US2010/057315, filed Nov. 19, 2010, which claims priority to European Patent Application No. 09176460.5, filed Nov. 19, 2009, the disclosures of which are herein incorporated by reference in their entirety.

FIELD OF THE INVENTION

The invention relates to a method in the preparation of a dental restoration, and in particular to a method of making a measuring element which is usable in the preparation of a dental restoration. The invention further relates to a system implementing the method, to a measuring element made by the method, and to a use of the measuring element.

BACKGROUND ART

A dental restoration is typically used to replace part of a natural tooth or even one or more entire natural teeth in a patient's mouth. A replacement of an entire tooth typically comprises a super structure, like a crown or a bridge, which typically is designed to resemble visible parts of a natural tooth. The tooth replacement typically further comprises a dental implant by which the replacement can be anchored in a patient's jaw. In many cases the super structure is connected to the dental implant via an abutment. Therefore such an abutment typically has an interface to the implant as well as a further interface to the super structure.

The dental implant is typically an elongated pin or screw which is inserted in a patient's jaw by surgery. After insertion the implant typically has to heal into the patient's jaw before the abutment and the super structure are placed on it. Typically the dental implant has a certain inclination angle in the patient's jaw to fit the anatomic situation in the patient's mouth, like for example the geometry of the gums and the jaw and their position relative to one another. On the other hand the super structure and/or the abutment may have to be angularly aligned to adjacent teeth so that the visible part of the final dental restoration is generally inline with such teeth. The angle required to fit with adjacent teeth may however be different from the angle of the implant. The abutment therefore may also provide for compensating such an angular offset.

To make the dental restoration fit nicely with adjacent teeth in a patient's mouth the abutment and/or the super structure is/are typically prepared by help of a physical model of the patient's teeth. Such a physical model typically also reproduces at least part of the inserted dental implant, for example an interface of the implant which is supposed to receive the abutment. Therefore a dental technician, for example, may physically shape and fit the abutment and/or the super structure into the desired place at the model.

The abutment and/or the super structure may also be prepared by using a CAD/CAM technique. In such a technique the shape of the physical model is typically captured by an optical measuring device. The so obtained computer model may then be used to design and manufacture the abutment and/or the super structure by computer aid. For the design of the abutment the shape of the implant interface is typically required in the form of computer data or a computer model. There are a variety of different implants on the market having dedicated uniquely shaped interfaces. Accordingly the implant manufacturers normally also provide computer models of at least the interfaces of their implants.

On the other hand in addition to the shape of the interface the actual position of the interface relative to other teeth in a patient's mouth is usually required to design the abutment and the super structure properly. For example the abutment and the super structure are usually designed to not only match with the interface of the implant, but also such that visible parts of the final dental restoration are positioned well inline with adjacent teeth.

In particular the inclination angle of the implant can typically not be provided by the implant manufacturer, but must be determined at the actual situation in a patient's mouth or at the physical model of the patient's teeth. To determine the inclination angle of the implant a measuring element is typically used. The measuring element is typically received on the interface of the implant and subsequently captured by the optical measuring device, like for example a three-dimensional scanner. The measuring element is typically shaped, for example elongated, such that its inclination angle can be determined from the captured shape. Some measuring elements also have a structure which indicates a rotational orientation, for example for use with implants having interfaces that require rotational positioning of the abutment to be received.

Because a measuring element must suit with a respective implant the implant manufacturers typically provide implant specific measuring elements.

Further the CAD software used to design the abutment and/or the super structure typically requires data about such a specific measuring element for recognizing the captured measuring element and for determining the angular position of the implant based thereon.

In summary the implant manufacturers typically have to provide data about the shape of the implant, data about the measuring element, and physical measure elements. On the other hand dental labs which use CAD/CAM methods for making tooth replacements based on several implant types typically purchase and maintain data libraries holding data about different implant types and measuring elements, and typically keep a stock holding a variety of physical measuring elements.

There are variations in the configuration of measuring elements, like one is disclosed in WO 2009/065954 A1. The document refers to a measuring body for an implant. The measuring body has a measuring geometry that can be captured by a measuring camera. Further the measuring body has a connection geometry for fitting on an implant. The measuring geometry and the connection geometry are separate parts. The same measuring geometry can be used with different connection geometries fitting different implants because the connection geometry and the measuring geometry have a unified interface with one another.

Although there are established approaches in the preparation of dental restorations there is still a need for facilitating the design of a dental restoration which is supposed to fit with a certain implant of a variety of different implants. It is further desirable to minimize the time period required to provide a dental restoration, and to provide a relatively inexpensive dental restoration that nevertheless has a relatively high quality.

SUMMARY OF THE INVENTION

The invention relates to a method in the preparation of a dental restoration of a type having an implant unit and a head structure which are adapted for interconnection with one another. The method comprises the steps of:

provining an auxiliary material;

providing a computerized head receiving surface representation (A') of a head receiving surface (A), the head receiving surface (A) being a surface of the implant unit for receiving the head structure;

manufacturing from the auxiliary material a measuring element having a measuring surface (M) and an implant unit coupling surface (X);

wherein the measuring surface (M) is adapted such that it can be captured by an optical measuring device; and wherein the measuring element coupling surface (X) is adapted for mating with the head receiving surface (A).

For the purpose of the invention an implant unit may comprise a dental implant and a dental link which are initially separate, but which can be interconnected. Further the implant unit may comprise the dental implant and the dental link in one piece. Although the one piece embodiment may in dentistry sometimes just be referred to as dental implant it is in this specification generally referred to as implant unit.

The method of the invention may be used for making a measuring element having a user-defined interface for coupling with an implant unit selected from a variety of different implant units. Thus the invention may be advantageous in that a dental lab may be enabled to work with different types of implant units without requiring a separate measuring element for each type. For example if the dental lab obtains the implant unit (or part of it) as a working sample from a dentist a measuring element may not necessarily accompanied with the sample. In this case the invention may allow the dental lab to nevertheless prepare an appropriate part of the dental restoration. Further the invention may help to minimize costs in the preparation of a dental restoration because the measuring element may not need to be purchased from an implant unit manufacturer. The measuring element may further be used to check the fit between the measuring element coupling surface and the head receiving surface. Thereby the fit between the implant unit and a head structure having a surface similar to the measuring element coupling surface may be simulated in advance. The invention may further provide for a relatively high precision of the dental restoration due to the preparation of the measuring element customized to a certain implant unit. The invention may also help minimizing time in the preparation of a dental restoration because the preparation of the dental restoration may be independent from a measuring element supplied from an implant unit manufacturer or supplier.

In one embodiment the measuring element coupling surface (X) and the head receiving surface (A) guide each other when mated such that the measuring element is held in a fixed position relative to the implant unit. For example the measuring element coupling surface (X) and the head receiving surface (A) may generally correspond in shape to one another and may further form a snug or tight fit with one another. The fit may for example include substantially no play between the measuring element coupling surface (X) and the head receiving surface (A). However the fit may still allow for manually mating and unmating of the measuring element and the implant unit.

In another embodiment the method further comprises the step of retrieving a computerized predetermined measuring surface representation (M") from a database. Such a database may hold a plurality of different predetermined measuring surface representations (M") belonging to different types of dental implant units. The method may further comprise the step of creating a computer model of the measuring element based on the predetermined measuring surface representation (M") and the head receiving surface representation (A'). For example the computer model of the measuring element may be created on a CAD system by combination of the predetermined measuring surface representation (M") and the head receiving surface representation (A'). The method may further comprise the step of modifying the computer model of the measuring element. For example the CAD system may be used to add, remove or change items of the computer model.

In a further embodiment the method comprises the steps of creating machine instructions for controlling a machine for manufacturing the measuring element based on the computer model of the measuring element. The method may further comprise the step of transmitting the machine instructions to a manufacturing machine for manufacturing the measuring element. Thus a separate machine for manufacturing of the measuring element may not be required.

In one embodiment the method of any of the preceding claims, wherein the manufacturing is based on material build-up and/or on material removal. The material removal may comprise at least one of milling, grinding, polishing and cutting. Further the material build-up may comprise at least one of laser sintering, and 3D-printing.

In one embodiment the method further comprises the step of physically providing the head receiving surface (A) of a corresponding dental implant unit. For example a dental implant unit may be provided physically to make the head receiving surface (A) available in a physical form. The step of providing the head receiving surface representation (A') may comprise measuring, in particular optical scanning, of at least a portion of the implant unit, in particular of the head receiving surface (A) of the implant unit. Thereby a sample a the implant unit may be sufficient to provide the head receiving surface representation (A'), and data from an implant unit manufacturer or supplier may not be required. Thus the invention may provide flexibility with regard to the use of different types of implant units.

On one embodiment the method further comprises the step of at least one of particle blasting, etching, and coating of at least part of the implant unit. Thereby an optically measurable head receiving surface (A) may be provided. For example a coated and/or roughed surface may be reliably recognizable by an optical measuring device.

In another embodiment the head receiving surface (A) is provided on a dental link which is also adapted for connection with a dental implant. The dental implant connected with the dental link preferably forms the dental implant unit. However the dental implant unit may comprise the dental implant, the dental ink and further components, like for example a screw for securing the dental link to the dental implant. A dental implant unit having an implant and a link component in the form of two pieces may be advantages in that the link may have properties different from the implant. For example the dental implant may be made of a material that is generally biocompatible, whereas the link may be made of a material providing for a durable connection with the head piece.

In one embodiment the auxiliary material is a plastic material. Therefore the measuring element may be manufactured relatively rapidly and inexpensively.

The so formed measuring element may be used in a measuring procedure for capturing the situation present in a patient's mouth.

In one embodiment the method comprises the step of placing the measuring element relative to an optical measuring device. The method may further comprise the step of placing the measuring element on a link of a dental implant unit. Further the method may comprise the step of capturing the measuring element by use of the optical measuring device. Thereby a computerized measuring surface representation (M') of the measuring device may be provided.

In a further embodiment the method comprises the step of determining at least one of an inclination angle and a rotational orientation of the measuring element. The inclination angle may be determined relative to a reference coordinate system of the measuring device and/or relative to a physical model of a patient's teeth. For example a plaster model of the patient's teeth may be provided at which a dental link or implant unit is attached at a position, inclination and orientation that corresponds to a position, inclination and orientation of the link when placed in the patient's mouth. This information may be used to make further parts of the dental restoration which precisely fit the situation in the patient's mouth.

In another embodiment the method comprises the step of matching the computerized measuring surface representation (M') with at least one computerized predetermined measuring surface representation (M"). The method may further comprise the step of selecting an appropriate predetermined measuring surface representation (M") from a plurality of predetermined measuring surface representations. Further the method may comprise the step of using the predetermined measuring surface representation (M") to determine the inclination angle and/or the rotational orientation of the measuring element. This may be performed by a computer algorithm which determines the relative position and/or the relative inclination angle and/or the relative rotational orientation between the measuring surface representation (M') and the selected predetermined measuring surface representation (M"). The use of the predetermined measuring surface representation (M") may facilitate the determination of the position and/or the inclination angle and/or rotational orientation of the measuring surface representation (M') because such information may be obtained from an alignment difference of the measuring surface representation (M') and the predetermined measuring surface representation (M") relative to one another, rather than from calculating such information based on only one surface representation. This may further save computing time.

The position and/or the inclination angle and/or rotational orientation of the measuring surface representation (M') may be used for designing parts of the head structure as described in the following.

In one embodiment the method comprises the step of providing information about the dental implant unit, like for example the type, and/or shape of at least portions of the dental implant unit. The method may further comprise the step of using the information about the dental implant unit to retrieve a computerized predetermined head receiving surface representation (A") from a database. For example if a head receiving surface representation (A') is present from optically measuring if the implant unit or dental link, a corresponding predetermined head receiving surface representation (A") may be retrieved from a database. Therefore the head receiving surface representation (A') may be conformed to the predetermined head receiving surface representation (A") to reduce tolerances from optically measuring, for example. The predetermined head receiving surface representation (A") may further be used in a similar manner for providing a measuring element coupling surface representation (X') used to form the measuring element coupling surface (X).

In another embodiment the method comprises the step of using the head receiving surface representation (A') for providing the information about the dental implant unit. For example the head receiving surface representation (A') may be used for comparing with a plurality of predetermined head receiving surface representations, and the predetermined head receiving surface representation which matches best in shape may be selected to retrieve associated information (like type and/or shape) about the dental implant unit. The method may further in particular comprise the step of matching the head receiving surface representation (A') with at least one predetermined head receiving surface representation to retrieve the predetermined head receiving surface representation (A") from a database.

In one embodiment the method comprises the step of creating a computer model of a dental abutment. The method may further comprise the step of providing the computer model of the abutment with a computerized implant unit receiving surface representation (B') based on at least one of the predetermined head receiving surface representation (A"), the inclination angle, and optionally the rotational orientation. Thus the abutment model may be provided with an interface for fitting on the implant unit, eventually accounting for an adhesive layer arranged between.

In another embodiment the method comprises the step of mating the measuring element with a head receiving surface (A) of a dental implant unit. The step may further comprise the step of evaluating the fit between the measuring element and the head receiving surface (A). This may allow for simulating the fit between the abutment and the implant unit without the presence of the abutment because the interface of the abutment to the implant unit may be similar to the interface of measuring element and the implant unit.

A further aspect of the invention relates to a measuring element comprising the measuring surface (M) and the implant unit coupling surface (X). The measuring element is of this aspect of the invention is obtained from the method according to the invention. Such a measuring element may be customized to a particular implant unit, and thus may provide for a better fit relative to pre-manufactured measuring devices of the prior art. Thus the invention may also allow for making a more precise dental restoration.

One aspect of the invention relates to a use of a measuring element to evaluate a fit between the measuring element and a head receiving surface (A) of a dental implant unit, in a situation where the measuring element is mated with the head receiving surface (A) of a dental implant unit. The measuring element comprises the measuring surface (M) and the implant unit coupling surface (X). Such a use may help reducing waste because a fit between an abutment and the implant unit may be simulated using the measuring element rather the abutment. In particular if the measuring element is made of a less expensive material than the abutment the invention thus also may help reducing costs during the preparation of a dental restoration.

Another aspect of the invention relates to a system for designing a dental restoration, wherein the system implements the method of the invention. Such a system may further comprise a computer, and/or a CAD software or function. Further the system may have a network and/or internet connectivity to obtain information, like type and/or shape, about a dental implant unit or parts of it. The system may further comprise a machine for manufacturing the measuring element and/or for manufacturing the dental restoration. The system may also provide a user interface for entering information about the dental implant unit. The user interface may allow for manually entering the information about the dental implant unit. Further the user interface may allow for entering information via data carrier and/or data readers. Thus the system may comprise a CAD/CAM sub-system. Such a system may facilitate the design and manufacturing of dental restorations or parts thereof, and thus may help to provide for a relatively inexpensive dental restoration which nevertheless is maximized in precision.

DETAILED DESCRIPTION OF THE INVENTION

The method in the making a dental restoration according to the invention may be generally described as having a determination phase and a design and manufacturing phase. The determination phase typically comprises steps of capturing information about a situation in a patient's mouth. Such information may for example include computer representations representing a shape of in a patient's mouth at an initial situation, and/or a situation in which a dental implant is placed in a patient's mouth. Further such information may include data about sizes, angles and/or orientations of a tooth, an implant, or parts of a dental restoration. Typically the information obtained in the determination phase is used in the design and manufacturing phase. For example the computer representations may be used to design dental restoration components such that they fit the situation in a patient's mouth.

For better understanding the dental restoration is described in its configuration first, and subsequently the determination phase and design and manufacturing phase are described.

Figure 1:
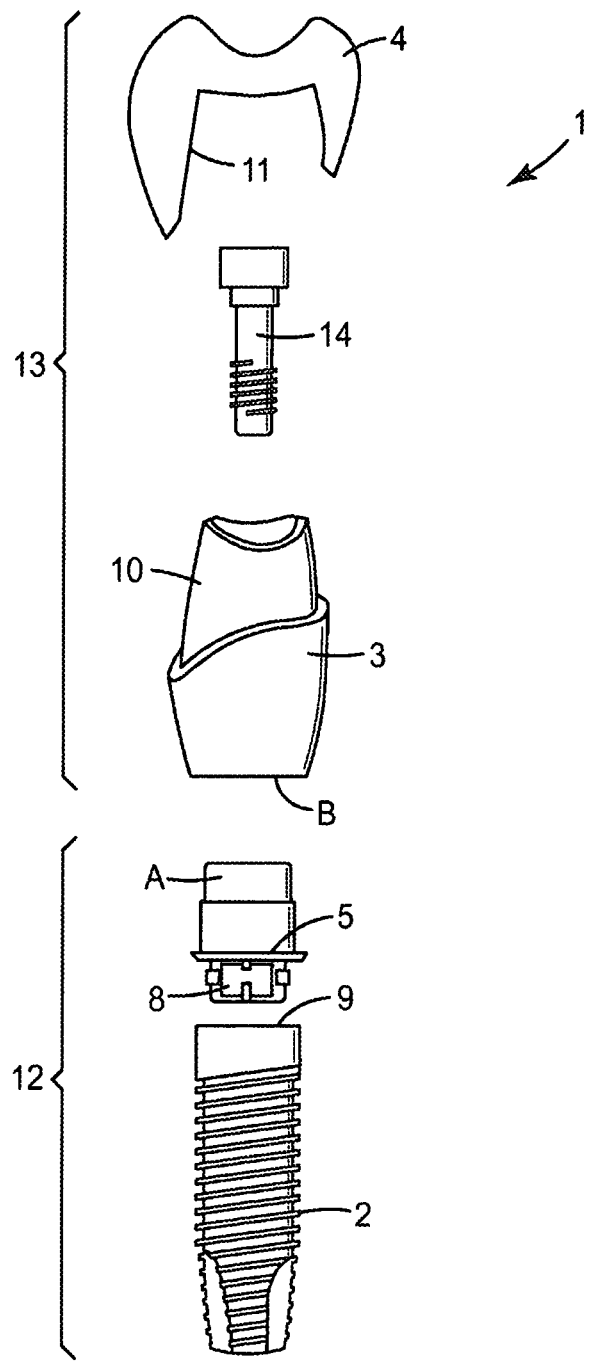
FIG. 1 is an exploded view of a dental restoration according to an embodiment of the invention.

FIG. 1 shows a dental restoration 1 as it may be used to replace an entire natural tooth in a patient's mouth. The illustrated dental restoration 1 basically has an implant unit 12 and a head structure 13. The implant unit 12 and the head structure 13 are adapted for interconnection with one another. Therefore the implant unit 12 has a head receiving surface A, and the head structure 13 has an implant receiving surface B (not visible). The head and implant receiving surfaces A, B are adapted to mate with one another. The shape of the head and implant receiving surfaces A, B may generally correspond to each other. Preferably the head and implant receiving surfaces A, B are substantially proportionally scaled relative to one another such that an adhesive layer can be arranged between.

In the example shown in FIG. 1 the implant unit 12 is formed by an implant 2 and a dental link 5 which form separate pieces. Such a configuration may for example be used to attach a ceramic based head structure to a metal implant. The implant 2 and the dental link 5 are adapted such that they can be connected with one another. Therefore the dental link 5 may have an implant connector 8 for connecting with a link connector 9 of the implant 2. The implant and link connectors 8, 9 are adapted to mate with one another, and may be further adapted to snap fit with one another. However in another example (not shown) the link may be part of the implant in which case the entire implant unit is formed by the implant only. Typically the implant is inserted in a patient's mouth first, and—after the implant has healed into the patient's jaw—subsequently completed to form the dental restoration.

The head structure 13 has an abutment 3 and a crown 4. The abutment 3 has an outer abutment surface 10 which is adapted to receive the crown 4. Accordingly the crown 4 has an inner crown surface 11 fitting with the outer abutment surface 10. For example the inner crown surface 11 and the outer abutment surface 10 may generally correspond in shape with one another. Further the inner crown surface 11 and the outer abutment surface 10 may be scaled proportionally relative to one another. Thus the inner crown surface 11 and the outer abutment surface 10 may be shaped such that a bonding layer (not shown) can be arranged between. The person skilled in the art will recognize that the abutment and the crown may in another example form one piece which may be veneered. Further the veneer may also be formed in one piece with the abutment and the crown. The bonding layer may for example have a generally uniform thickness, or may taper off toward its outside boundaries. Such a bonding layer may for example comprise a dental luting cement. The crown 4 may further comprise a framework and a veneer (not shown in detail). In this case the framework may be basically a supporting structure for providing a certain mechanical stability for the dental restoration, whereas the veneer may provide for pleasing aesthetic characteristics.

The dental restoration 1 further has a screw 14 for mounting the link 5 onto the implant 2. In the example shown the dental restoration 1 is adapted such that the screw 14 can extend through the abutment 3 and the link 5 into the implant 2. In particular the abutment 3 and the link 5 each have a through hole through which the screw 14 can extend. Thus the link 5 may be affixed to the abutment 3 first and the so formed assembly may be subsequently secured on the implant unit 12.

The implant unit 12 may be standardized and made available to dentists for use in a patient's mouth. Further the head structure 13 may be individually prepared by a dental lab to fit a certain implant unit and a certain situation in a patient's mouth. The implant unit 12 and the head structure 13 may then be merged, for example by the dentist, to form the dental restoration. A method in the preparation of the dental restoration according to an embodiment of the invention is described in the following.

Figure 2:
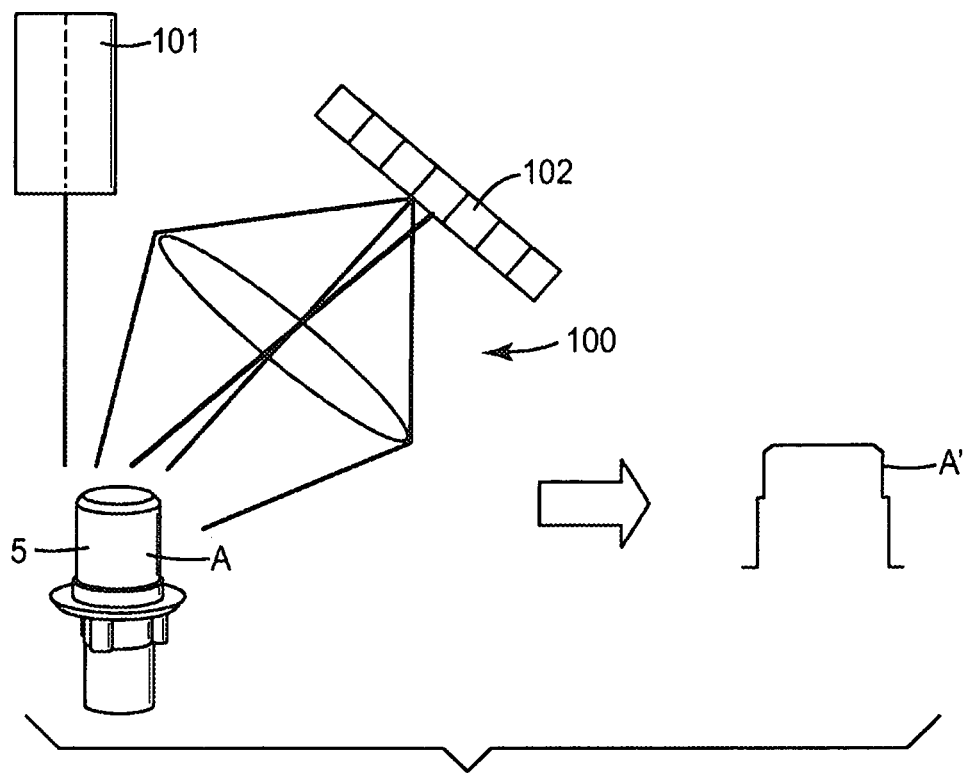
FIG. 2 is a schematic view illustrating a method step of capturing a head receiving surface according to an embodiment of the invention.

FIG. 2 illustrates a method step of the determination phase in which the dental link 5 is measured to provide a computerized head receiving surface representation A'. The link 5 has a head receiving surface A which forms an interface for receiving the head structure of the dental restoration. Therefore the shape of the head receiving surface A is captured by an optical measuring device 100 (not shown in all detail) to make it available for further steps in the preparation of the dental restoration. For this purpose the dental link 5 is placed in the optical measuring device 100. The illustrated optical measuring device is a light scanner which has a projector 101 for illuminating an object (in the example the dental link 5) with a point or a light pattern (not illustrated), for example with light stripes. The optical measuring device further has a CCD camera 102 for capturing the image of the illuminated object. The object is typically captured from different angles and/or orientations. The captured images are then used to create a three-dimensional computer representation of the object in the form of surface data. In the example the measuring device is used to capture the head receiving surface A to form the head receiving surface representation A'. The head receiving surface representation A' can be transmitted to a computer, for example one having a CAD system installed, where it can be further processed.

Figure 3:
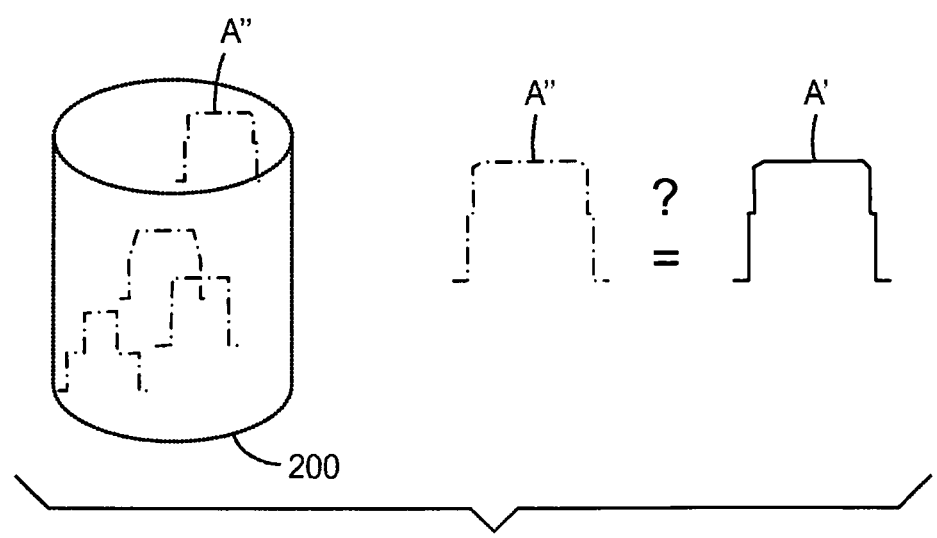
FIG. 3 is a schematic view illustrating a method step of matching a head receiving surface representation with a pre-determined head receiving surface representation according to an embodiment of the invention.

FIG. 3 illustrates an optional method step in which the head receiving surface representation A' is matched with at least one computerized predetermined head receiving surface representation to retrieve a computerized predetermined head receiving surface representation A". This method step may be generally used to verify a scanned surface with a predetermined surface to conform the scanned surface to a more precise predetermined surface, or to replace the scanned surface by the predetermined surface. Thereby a better precision in the preparation of the dental restoration may be achieved.

This method step may be performed on the CAD system, or on another computer, for example. The computer may have a database 200 holding a plurality of different predetermined head receiving surface representations. Such predetermined head receiving surface representations may for example be provided by suppliers and/or manufacturers of dental implant units in the form of data. Therefore the database may contain a plurality of predetermined head receiving surface representations for different types (sizes and/or shape) of implants of the same supplier/manufacturer, and/or predetermined head receiving surface representations of implants of different suppliers/manufacturers.

The matching in the example comprises comparing the head receiving surface representation A' with at least one predetermined head receiving surface representation contained in the database 200. The matching further may comprise identifying the predetermined head receiving surface representation A" based on the comparison with the head receiving surface representation A', for example due to the head receiving surface representation A' and the predetermined head receiving surface representation A" best match in shape.

The so identified predetermined head receiving surface representation A" may optionally be proposed to a user who can accept or reject the predetermined head receiving surface representation A" for further processing. For example the head receiving surface representation A' may be replaced by or conformed to the predetermined head receiving surface representation A". This may be of advantage if for example the head receiving surface representation A' was obtained by scanning as illustrated in FIG. 2. In that case the scanned head receiving surface representation A' may have tolerances and may therefore lack sufficient precision for a direct use in the preparation of the dental restoration. However the scanned head receiving surface representation A' may be sufficiently precise to select a more precise predetermined head receiving surface representation A" from the database which is then used for further processing. In any event the head receiving surface representation obtained from this method step is referred to as A' in the following although the head receiving surface representation may correspond to the predetermined head receiving surface representation A" in some instances.

In an alternative method step (not illustrated) the head receiving surface representation A' may be provided from a database dependent on a user input. The computer may therefore have a user interface via which such data can be entered, for example via keyboard, by a data carrier, via a data capturing device, like a bar code or RFID reader, or in any other appropriate manner.

Further the head receiving surface representation A' obtained from measuring, in particular from scanning, may be directly used for the further preparation of the dental restoration.

Figure 4:
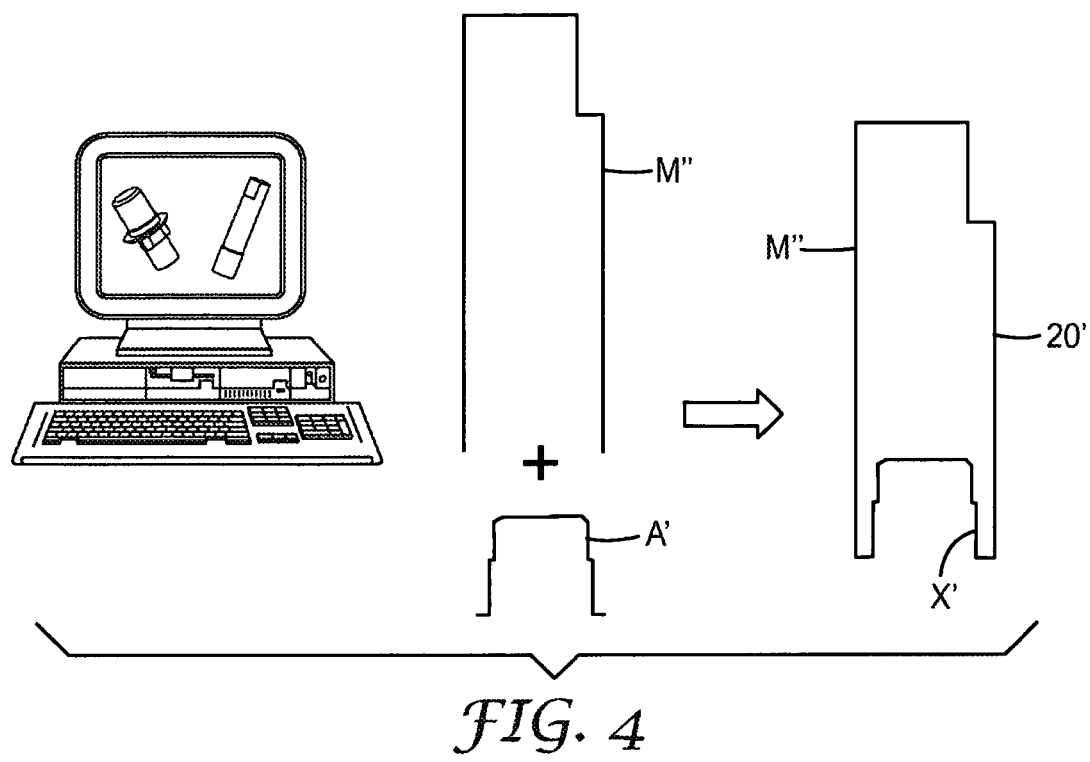
FIG. 4 is a schematic view illustrating a method step of designing a measuring element according to an embodiment of the invention.

FIG. 4 illustrates a further method step in which the head receiving surface representation A' is combined with a predetermined measuring surface representation M" to form a computer model 20' of a measuring element. The measurement element is typically not a part of the dental restoration, but an auxiliary element used during preparation of the dental restoration. The measuring element is preferably attached onto an implant unit and is sized, shaped and otherwise adapted such that it can be measured more easily and precisely by a measuring device than the implant unit itself. For example the implant unit may be relatively small, or may not have a surface that suitable for optical measuring, or may be located inappropriately for optical measuring, so that appropriate optical measuring may be only possible using a measuring element.

The computer model 20' of the measuring element may be created by using a standardized predetermined measuring surface representation M" stored on the computer and adding an individual head receiving surface representation, like for example one as obtained in the step illustrated in FIG. 2. The computer model 20' of the measuring element may be in particular created automatically by the computer based on the head receiving surface representation A', and the predetermined measuring surface representation M". Further the computer may provide CAD functionality so that a user may add or change design features of the measuring element model. The computer model of the measuring element in the example shown obtains an implant unit coupling surface representation X' with is adapted for mating with the head receiving surface A (shown in FIG. 2). Therefore the implant unit coupling surface representation X' may generally correspond to the head receiving surface representation A'. Further the implant unit coupling surface representation X' may be scaled, for example enlarged, proportionally relative to the head receiving surface representation A'. This may provide for a certain dimensional allowance that may facilitate placement of the finished measuring element onto the head receiving surface.

Figure 5:
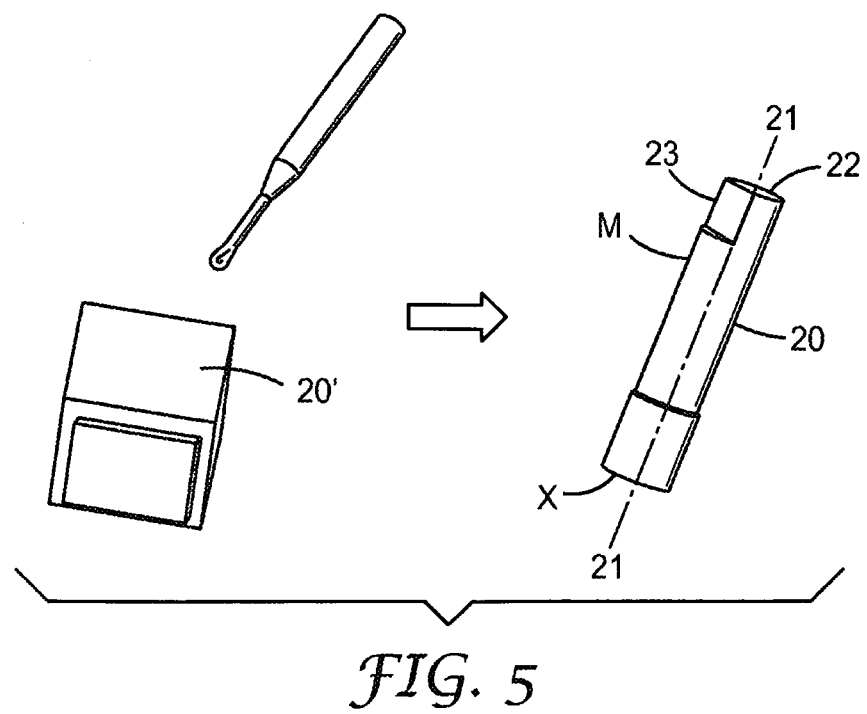
FIG. 5 is a schematic view illustrating a method step of making a measuring element according to an embodiment of the invention.

FIG. 5 illustrates a step of manufacturing the measuring element 20 from an auxiliary material 20'. The auxiliary material 20' in the example is in the form of a blank which is shaped by material removal, for example grinding, cutting or milling. The auxiliary material may be wax, plastic material, or ceramics, for example. For the manufacturing of the measuring element 20 a dental milling machine may for example be used. Therefore the user may save an additional machine for manufacturing of the measuring element. Further the measuring element may be manufactured by build-up processes, like for example laser sintering, or 3D-printing. A build-up machine for manufacturing dental restorations may also be used for manufacturing of the measuring element. The measuring element 20 has a measuring surface M and an implant unit coupling surface X (not visible). The implant unit coupling surface X is adapted to mate with (for example to form a tight fit with) the head receiving surface A (shown in FIG. 2).

The measuring element in the example extends along a measuring element axis 21 between the implant unit coupling surface X and an opposite free end 22. The implant unit coupling surface X is shaped such that, when mated with the dental link (not shown), is retained on the link. In the example shown the implant unit coupling surface X forms a socket for snugly or tightly fitting with the head receiving surface of the link.

Further the measuring element 20 may have an orientation feature 23 which in the example shown is a flat arranged adjacent the free end 22 and generally parallel to the measuring element axis 21. The implant unit coupling surface X may also have an orientation feature which may lock or retain with an orientation feature of the dental link. Therefore the measuring element may be used to determine a rotational orientation about the measuring axis. The rotational orientation of the measuring element may then be used to determine a rotational orientation of the dental link and/or the implant unit about the measuring axis. This may facilitate rotationally aligning a head structure with the implant unit, and may help to provide a dental restoration which pleasantly fits the situation in a patient's mouth.

Figure 6:
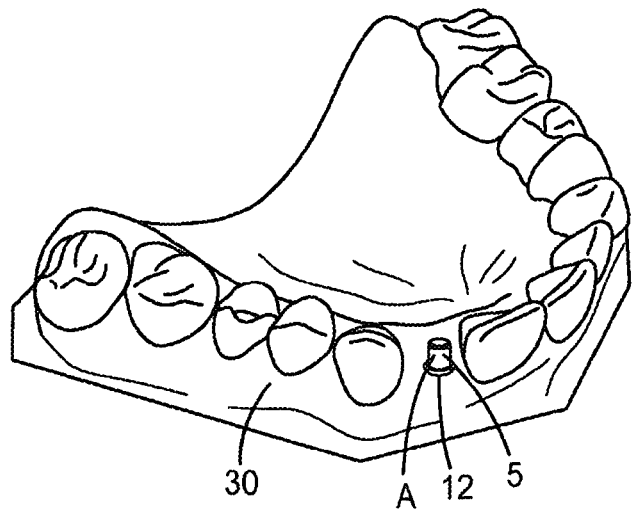
FIG. 6 is a schematic view of a physical model of a patient's jaw which has an implant unit according to an embodiment of the invention.

FIG. 6 shows a physical model 30 of a patient's jaw having an implant unit 12 having a link 5. The physical model 30 represents the situation in a patient's mouth including the implant unit 12 inserted in the jaw. The model may be a plaster model for example which represents at least the head receiving surface A of a dental link 5 (FIG. 1).

Figure 7:
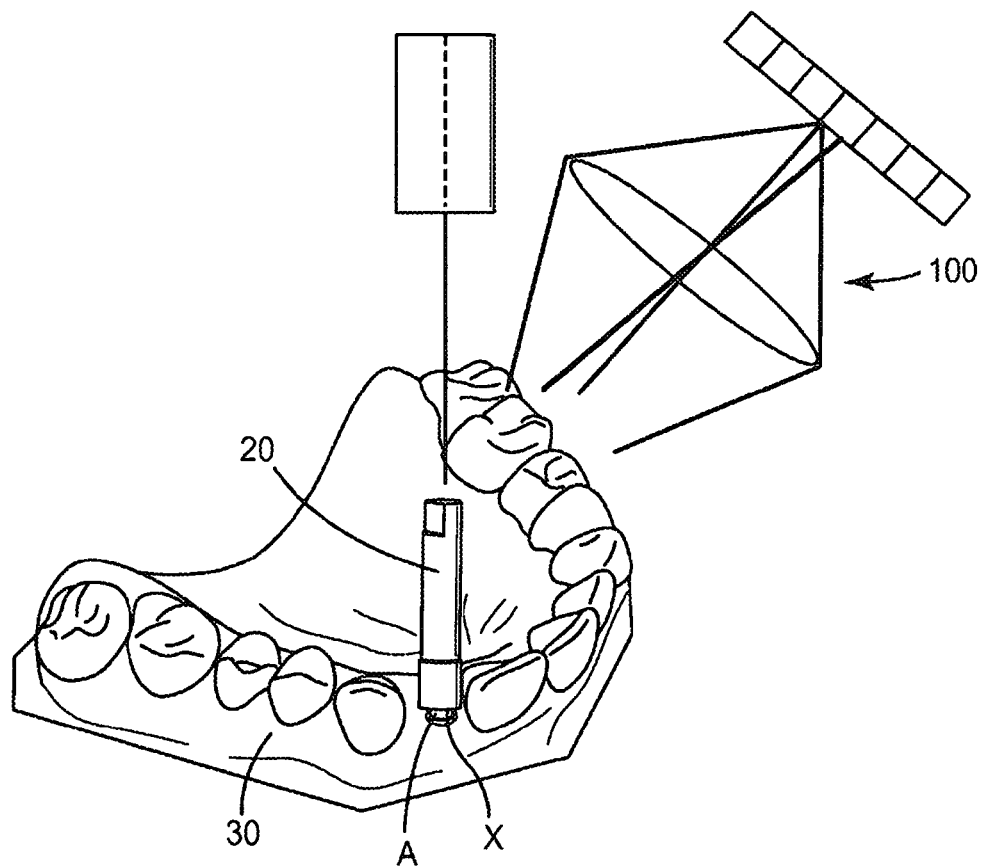
FIG. 7 is a schematic view illustrating a method step of capturing the physical model and the measuring element according to an embodiment of the invention.

FIG. 7 illustrates a method step of preparing the dental restoration. The measuring element 20 is placed on the head receiving surface A in the physical model 30. In particular the implant unit coupling surface X is mated with the head receiving surface A. Due to the shape and matching of the implant unit coupling surface X and the head receiving surface A the measuring element 20 is held in a defined position relative to the head receiving surface A.

The physical model 30 with the measuring element 20 are placed in the measuring device 100, for example one as described in FIG. 2. The physical model 30 and the measuring element 20 are optically captured. Because of the defined positioning of the measuring element relative to the head receiving surface A the inclination angle of the measuring element can be determined relative to the patient's jaw. This is described in more detail in FIG. 8.

Figure 8:
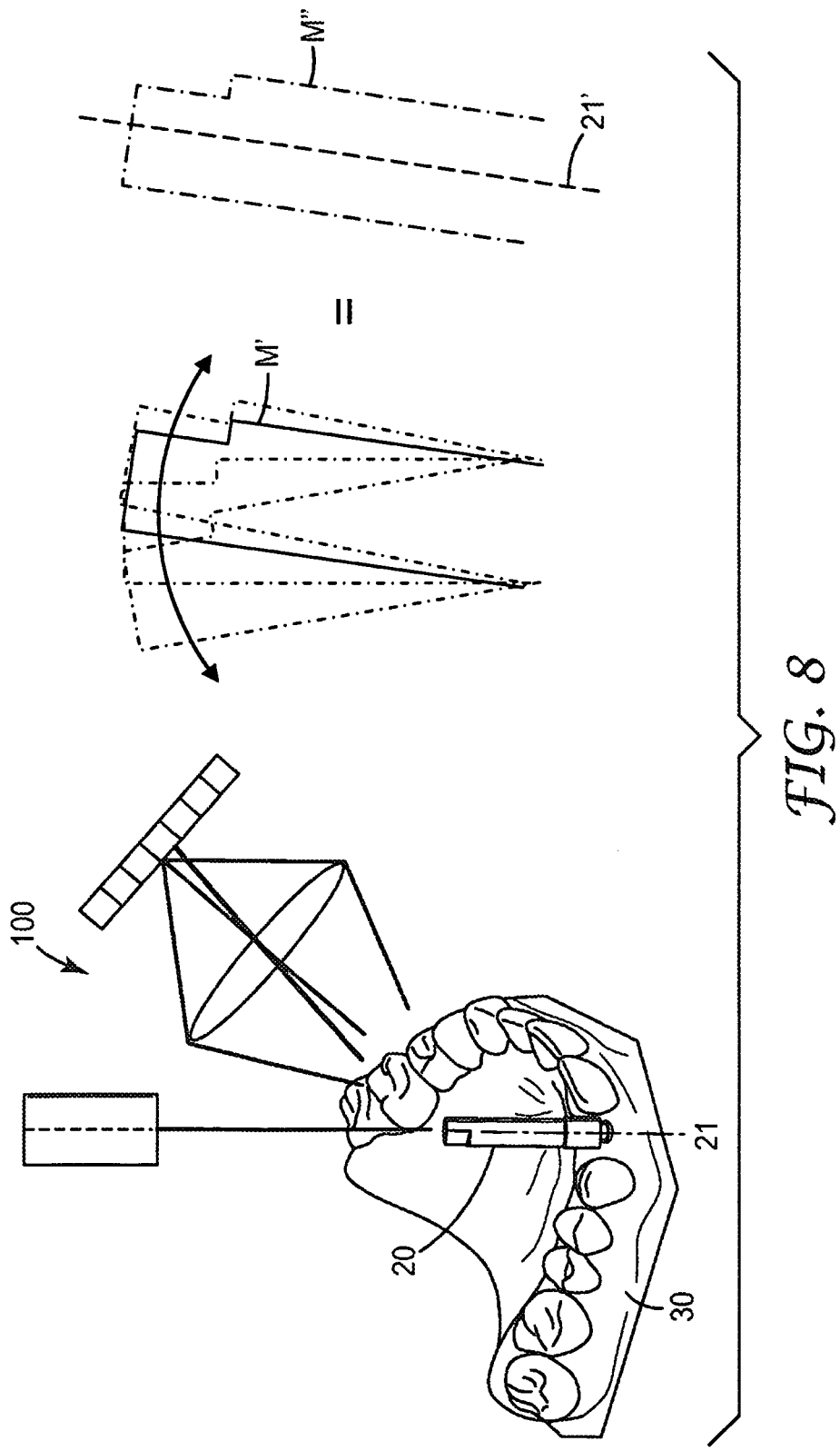
FIG. 8 is a schematic view illustrating a method step of matching a measurement surface representation with a pre-determined measurement surface representation according to an embodiment of the invention.

FIG. 8 illustrates a method step in which the measuring element 20 is captured by the measuring device 100 and in which an inclination angle of the implant unit in the patient's mouth is derived from. In the method step a computerized measuring surface representation M' is obtained, for example by optically measuring or scanning using the measuring device 100. The measuring surface representation M' may be transmitted to a computer and directly used to determine an inclination angle of the measuring element, for example by calculating the center axis of the measuring element using a computer algorithm.

From the inclination angle of the measuring element the inclination angle of the implant unit may be derived because the relationship between the inclination angle of the measuring element and the inclination angle of the implant unit is preferably predefined. In the Figure the inclination angle of the implant unit is indicated as inclination angle 21.

Further the inclination angle of the measuring element may be determined by matching the measuring surface representation M' with a predetermined measuring surface representation M". The predetermined measuring surface representation M" may have an inclination axis representation 21' which has a defined position and inclination angle relative to the predetermined measuring surface representation M". Therefore the matching may comprise aligning the surfaces M' and M" with one another such that the position and inclination of both match best. This may not necessarily be done visually as illustrated, but mathematically only. Once the alignment of the predetermined measuring surface representation M" relative to the measuring surface representation M' is determined the position and/or inclination of the axis representation 21' can be directly derived from the dataset defining the predetermined measuring surface representation M". This may save time for calculating the position and inclination angle of the measuring axis 21. A similar principle may be used to determine a rotational orientation of the measuring element 20.

The predetermined measuring surface representation M" may be selected from a database by a user, or by matching with at least one predetermined measuring surface representation in the database, similar to the method shown in FIG. 3.

The skilled person will recognize other mathematical principals to determine the position and inclination of the measuring element. From the position and inclination of the inclination axis 21' the position and inclination of the inclination axis 21 may be derived. Preferably the inclination axes 21, 21' are generally in line.

In FIGS. 1 to 8 the determination phase has been described, in which further a measuring element is prepared. The following description refers to the preparation of particularly the head structure of the dental restoration, and thus to the design and manufacturing phase of the method of the invention. It is noted that although the examples refer to a crown as part of the head structure other dental super structures are included, like for example a bridge.

Figure 9:
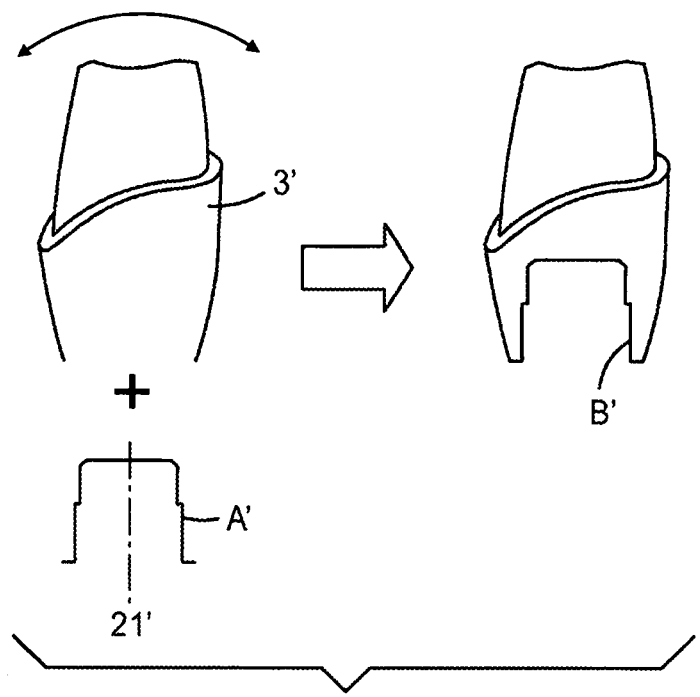
FIG. 9 is a schematic view illustrating a method step of designing an abutment according to an embodiment of the invention.

FIG. 9 illustrates a method step in which a computer model 3' of an abutment is provided. For example the computer model 3' of the abutment may be obtained from a database holding a plurality of differently shaped and/or sized computer models. Further the head receiving surface A' is combined with the computer model 3' of the abutment to form a completed computer model of the abutment. Thereby the head receiving surface representation A' is preferably aligned to the inclination axis 21' determined in the step shown in FIG. 8. Thus the finished abutment may be adapted to fit with the inclination angle of the implant unit.

The head receiving surface representation A' may be used to form a computerized implant unit receiving surface representation B' in the abutment model. The head receiving surface representation A' and the implant unit receiving surface representation B' may for example generally correspond in shape, however may further be scaled proportionally relative to one another. Thus a gap may be provided between the abutment and the implant unit allowing for accommodation of a bonding layer between. The so created completed computer model of the abutment may be transmitted to a dental manufacturing machine in which the abutment is manufactured.

Figure 10:
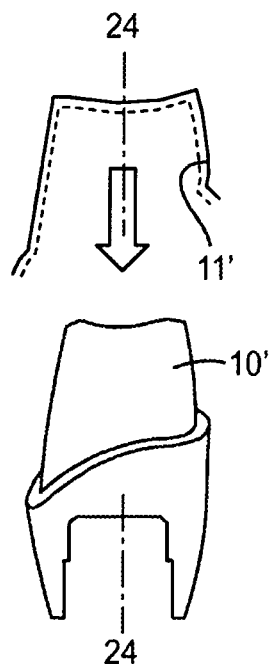
FIG. 10 is a schematic view illustrating a method step of designing an inner surface of a crown according to an embodiment of the invention.

FIG. 10 illustrates a further method step in which an outer abutment surface representation 10' is used to determine an inner crown surface 11'. The outer abutment surface representation 10' and the inner crown surface 11' may define a placement direction which is a direction in which the crown and the abutment can be moved toward one another for assembly. The placement direction may be defined by a placement axis 24 which may be inclined relative to the inclination axis of the implant unit. Thus the abutment may compensate for an inclination between the placement axis and the inclination axis of the implant unit. As indicated by the dashed line relative to the solid line in the Figure the inner crown surface representation 11' may be enlarged generally proportionally relative to the outer abutment surface representation 10'. This may allow accommodation of a bonding material (for example a dental luting cement) between the abutment and the crown.

Figure 11:
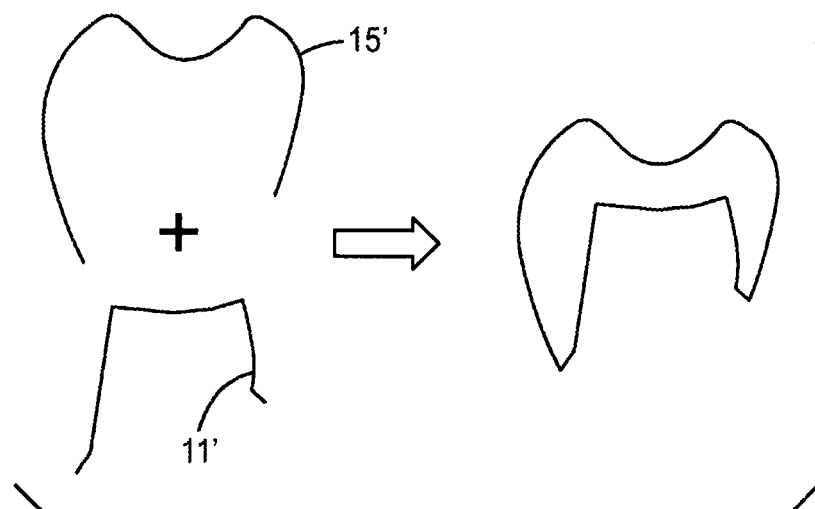
FIG. 11 is a schematic view illustrating a method step of designing a crown according to an embodiment of the invention.

FIG. 11 illustrates a method step in which the inner crown surface representation 11' is combined with an outer crown surface representation 15' to form a computer model of a crown. Such an outer crown surface representation 15' may represent an outer surface of a framework, or an outer or inner surface of a veneer, for example. The skilled person will recognize methods to create other surface representations as desired based on one or more surface representations created according the method steps of the invention. The computer model of a crown may then be transmitted to a dental manufacturing machine in which the crown is manufactured.

Figure 12:
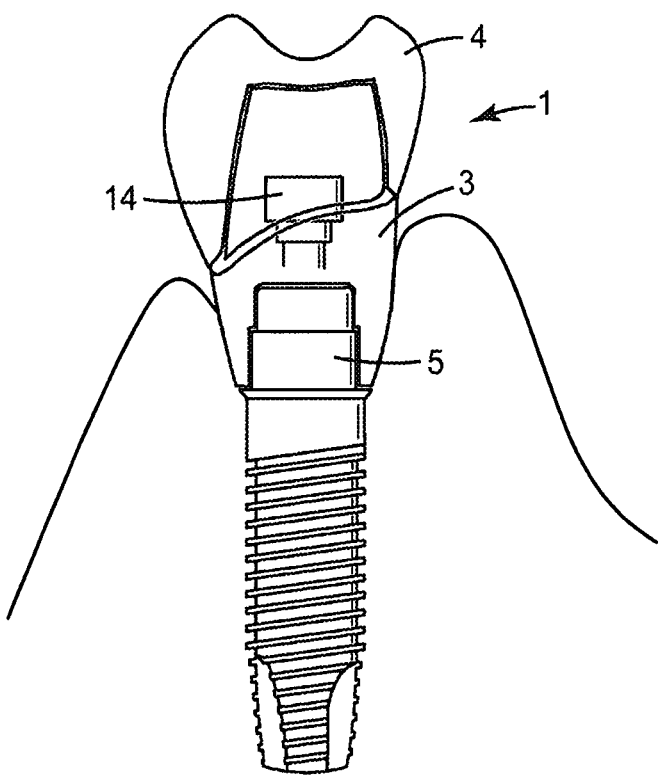
FIG. 12 is a cross-sectional view showing a patient's jaw and the dental restoration according to an embodiment of the invention.

FIG. 12 shows the dental restoration 1 when assembled and placed in a patient's mouth. Typically a dentist assembles the abutment 3 (eventually together with the dental link 5, if present as separate piece) to the implant by use of the screw 14. An adhesive may be provided between the link 5 and the abutment 5. Thus the implant unit and the head structure may be mechanically secured with one another. Further the interconnection between the implant unit and the head structure may be sealed against penetration of substances. Therefore for example bacteria may be prevented from penetrating between the implant unit and the head structure. This may help maximizing the durability of the dental restoration. The dentist may subsequently assemble the crown 4 on the abutment 3, for example by use of a luting cement. Thus the crown and the abutment may be sealingly secured with one another. Substances and/or bacteria may therefore be prevented from penetrating between the crown 4 and the abutment 3. This also may help maximizing the durability of the dental restoration.

The invention claimed is:

1. A method in the preparation of a dental restoration, the dental restoration having an implant unit and a head structure which are adapted for interconnection with one another, the method comprising:
   providing an auxiliary material;
   providing a computerized head receiving surface representation (A') of a head receiving surface (A), the head receiving surface (A) being a surface of the implant unit for receiving the head structure;
   manufacturing from the auxiliary material a measuring element having a measuring surface (M), an implant unit coupling surface (X), a measuring axis, and an orientation feature;
   retrieving a computerized predetermined measuring surface representation (M") from a database;
   creating a computer model of the measuring element based on the computerized predetermined measuring surface representation (M") and the computerized head receiving surface representation (A');
   placing the measuring element relative to an optical measuring device;
   capturing the measuring element by use of the optical measuring device to provide a computerized measuring surface representation (M') of the measuring device;
   determining an inclination angle and a rotational orientation of the measuring element; and
   aligning the measuring surface representation (M') with the predetermined measuring surface representation (M") such that a position and inclination angle of the measuring surface representation (M') matches a position and inclination angle of the predetermined measuring surface representation (M");
   wherein the measuring surface (M) is adapted such that it can be captured by an optical measuring device;
   wherein the measuring element coupling surface (X) is adapted for mating with the head receiving surface (A); and
   wherein the orientation feature can be used to determine a rotational orientation of the measuring element about the measuring axis.

2. The method of claim 1, further comprising:
   creating machine instructions for controlling a machine for manufacturing the measuring element based on the computer model of the measuring element; and
   transmitting the machine instructions to a manufacturing machine for manufacturing the measuring element;
   wherein the manufacturing is based on material build-up and/or on material removal.

3. The method of claim 1, further comprising physically providing the head receiving surface (A) of a corresponding dental implant unit, and wherein providing the computerized head receiving surface representation (A') comprises optical scanning of at least a portion of the head receiving surface (A).

4. The method of claim 3, further comprising at least one of particle blasting, etching, and coating of at least part of the implant unit to provide an optically measurable head receiving surface (A).

5. The method of claim 3, in which the head receiving surface (A) is provided on a dental link which is adapted for connection with a dental implant, wherein the dental implant connected with the dental link form the dental implant unit.

6. The method of claim 1, further comprising:
   providing information about the dental implant unit; and
   using the information about the dental implant unit to retrieve a computerized predetermined head receiving surface representation (A") from a database.

7. The method of claim 6, further comprising:
   using the computerized head receiving surface representation (A') for providing the information about the dental implant unit; and
   matching the computerized head receiving surface representation (A') with at least one computerized predetermined head receiving surface representation to retrieve the computerized predetermined head receiving surface representation (A") from a database.

8. The method of claim 6, further comprising:
   creating a computer model of a dental abutment; and
   providing the computer model of the abutment with a computerized implant unit receiving surface representation (B') based on at least one of the computerized predetermined head receiving surface representation (A"), the inclination angle, and the rotational orientation.

9. The method of claim 1 further comprising:
   mating the measuring element with a head receiving surface (A) of a dental implant unit;

evaluating the fit between the measuring element and the head receiving surface (A).

10. A measuring element obtained from the method according to claim 1, the measuring element having a measuring surface (M) and an implant unit coupling surface (X), wherein the measuring surface (M) is adapted such that it can be captured by an optical measuring device, and wherein the measuring element coupling surface (X) is adapted for mating with a head receiving surface (A) of a dental implant unit.

11. A system for designing a dental restoration, implementing the method of claim 1, the system comprising a computer, a user interface for entering information about the dental implant unit, and a machine for manufacturing the measuring element.

12. The method of claim 1, wherein the manufacturing step comprises providing as the orientation feature a flat adjacent an end of the measuring element opposite the implant unit coupling surface (X) and generally parallel to the measuring axis.

* * * * *